United States Patent [19]

Salamone

[11] 4,401,650

[45] Aug. 30, 1983

[54] SKIN CONDITIONING POLYMERS CONTAINING ALKOXYLATED NITROGEN SALTS OF SULFONIC ACID

[75] Inventor: Ann B. Salamone, Marblehead, Mass.

[73] Assignee: Thiokol Corporation, Chicago, Ill.

[21] Appl. No.: 302,324

[22] Filed: Sep. 15, 1981

[51] Int. Cl.³ .................. A61K 31/74; A61K 31/78
[52] U.S. Cl. .................................... 424/78; 424/81; 525/286
[58] Field of Search ............... 424/78, 81; 525/1, 286

[56] References Cited

U.S. PATENT DOCUMENTS 3,395,215 7/1968 Schubert et al. .................. 424/81
4,065,422 12/1977 Lundmark et al. ................ 424/73
4,128,631 12/1978 Lundmark et al. ................ 424/78

FOREIGN PATENT DOCUMENTS 864433 2/1971 Canada .

Primary Examiner—Delbert R. Phillips
Assistant Examiner—F. T. Moezie
Attorney, Agent, or Firm—Gerald K. White

[57] ABSTRACT

Polymers containing alkoxylated nitrogen salts of sulfonic acids are useful for imparting good conditioning properties such as improved feel to skin, and skin irritation reduction, and humectancy. The polymers may also comprise neutral, anionic, and/or cationic monomers.

22 Claims, No Drawings

SKIN CONDITIONING POLYMERS CONTAINING ALKOXYLATED NITROGEN SALTS OF SULFONIC ACID

BACKGROUND OF THE INVENTION

This invention generally pertains to a polymer useful for imparting good conditioning properties to skin. The polymer comprises an ethylenically unsaturated addition polymerizable monomer containing an alkoxylated nitrogen salt of sulfonic acid. The polymers may also include neutral, anionic, and/or cationic monomers. Skin conditioning products generally are considered to function to improve such properties as retention of skin moisture, softening of skin, attraction of air moisture, retardation of skin water loss, feel and reduction of skin irritations caused by contact with detergents, soaps and the like. Historically, two broad areas of skin care products could be considered as skin conditioners: Emollients and Humectants. Emollients function to provide improved moisture retention in the skin and plasticization/softening of the skin. Common commercial emollients are mineral oil; petrolatum; aliphatic alcohols, such as stearyl alcohol; lanolin and its derivatives; glycol stearate; and fatty acids, such as triethanolamine oleate. Humectants function to attract moisture, retard evaporation of $H_2O$ from the skin surface, and plasticize/soften skin. Common commercial humectants are glycerin, propylene glycol, sorbitols, and polyethylene glycols.

A desirable skin conditioner should impart all or some of the attributes of an emollient and a humectant, as well as provide an improved feel to the skin after treatment and/or reduce skin irritation caused by other components in the conditioner such as soaps, detergents, foam boosters, surfactants perfumes and the like. Recently, cationic polymers have been used as skin conditioners. The two most often used are Merquat 550 from Merck-poly(acrylamide-(co) diallyl dimethyl ammonium chloride) and Polymer JR from Union Carbide—a quaternary nitrogen-containing hydroxyethyl cellulose.

One patented product is similar to the compound(s) of interest here, but not equivalent in chemical structure or skin conditioning properties. U.S. Pat. Nos. 4,065,422 and 4,128,631 are directed to personal care products which serve to impart a feeling of lubricity on keratinous surfaces. These homopolymer products contain high molecular weight polymeric salts of 2-acrylamido-2-methylpropane sulfonic acid (AMPS). Such AMPS homopolymers have a molecular weight ranging from 1 to 5 million.

The polymer of the invention is believed to constitute a very significant improvement in the skin conditioning art because such polymer, when contrasted to the products mentioned above, exhibits a superior combination of skin care properties. These properties include improved moisture retention, and improved feel of the skin during and after treatment.

SUMMARY OF THE INVENTION

The polymer of the invention has been found to impart excellent feel, softening to the skin, and improved air moisture attraction, hence, such polymers are advantageous incorporated into various skin conditioning products. These polymers are generally classified as polyanionics; i.e., polymers which contains sulfonic acid groups neutralized with an alkoxylated nitrogen-containing compound. Such alkoxylated nitrogen-containing compound may conveniently be an ethoxylated amine or ethoxylated quaternary ammonium salt. The polymer includes at least one ethylenically unsaturated addition polymerizable monomer containing an alkoxylated nitrogen salt of sulfonic acid and may also include additional monomers that may be neutral, anionic and/or cationic.

Sulfonic acid containing polymers as described herein are neutralized with ethoxylated quaternary ammonium salt or ethoxylated amines to form the desired polymer of the invention. Neutralization may be effected to proportions between about 10 to 100 mole % to be employed in the practice of the invention. A range of about 25 to 100 mole % is preferred. Neutralization with an ethoxylated quaternary ammonium salt is generally depicted as follows:

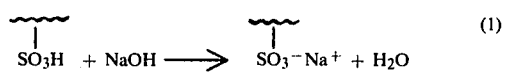   (1)

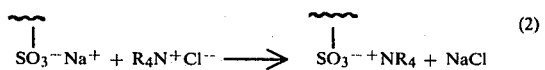   (2)

Neutralization with an ethoxylated amine is generally depicted as follows:

A concentration range of from about 0.1 to 10 wt % of the polymer of the invention has been found to be useful in skin conditioners such as hand lotions and the like. A concentration on the order of about 1.0 wt % is preferred. For other types of skin care formulations, the amount required will vary depending upon the type of treatment and quality of the skin.

Nitrogen salts of sulfonic acids include alkoxylated quaternary ammonium salts, alkoxylated amines and admixtures thereof. Quaternary ammonium salts suitable for use in the invention have the following general structure:

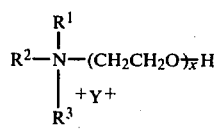

where, $R^1, R^2, R^3$ = H,
    alkyl ($C_1$-$C_{30}$),
    aryl,
    $(CH_2CH_2O)_{\overline{x}}H$, or
$R^1$—$R^2$ = cycloalkylene, where, $Y^-$ = halide, sulfate, etc., and
    x = 1 to 50

Suitable examples of alkoxylated quaternary ammonium salts include:

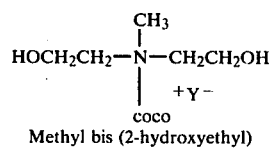

Methyl bis (2-hydroxyethyl)

-continued
coco ammonium salt

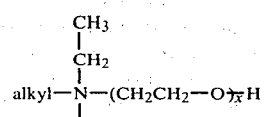

Ethyl bis (polyhydroxyethyl)
alkyl ammonium salt

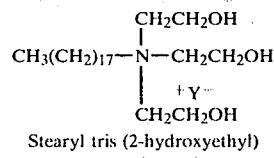

Stearyl tris (2-hydroxyethyl)
ammonium salt

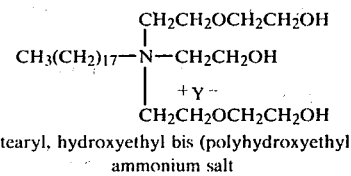

Stearyl, hydroxyethyl bis (polyhydroxyethyl)
ammonium salt

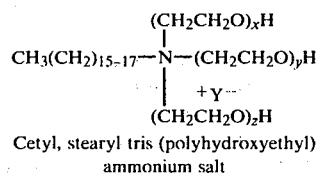

Cetyl, stearyl tris (polyhydroxyethyl)
ammonium salt

Alkoxylated amines suitable for use in the invention have the following general structure:

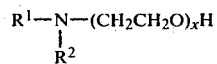

where, $R^1$, $R^2$, = H,
    alkyl ($C_1$-$C_{30}$),
    aryl,
    $(CH_2CH_2O)_xH$, or
$R^1$—$R^2$ = cycloalkylene, and $x = 0.1$ to 50

Suitable examples of alkoxylated amines include the following compounds:

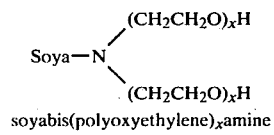

soyabis(polyoxyethylene)$_x$amine

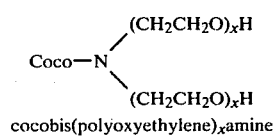

cocobis(polyoxyethylene)$_x$amine

-continued

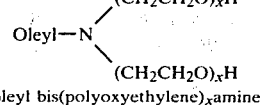

oleyl bis(polyoxyethylene)$_x$amine

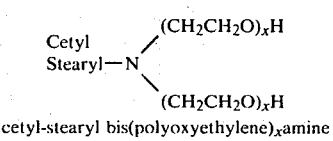

cetyl-stearyl bis(polyoxyethylene)$_x$amine

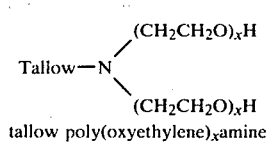

tallow poly(oxyethylene)$_x$amine

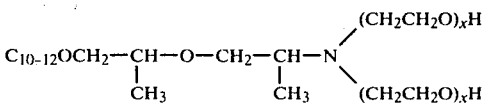

Soya bis(polyoxyethylene)$_{15}$amine is an example of a particularly suitable ethoxylated amine salt.

Although the polymer of the invention may consist entirely of the product produced by the polymerization of ethylenically unsaturated monomer containing an alkoxylated nitrogen salt of sulfonic acid, an additional monomer may be utilized. The additional monomer (or monomers) does not add or detract from the unique properties and advantages of the sulfonic acid type polymer, but is utilized to reduce the cost of the polymer. Such polymers may be produced through vinyl polymerization monomers containing sulfonate. Such monomers include 2-acrylamido-2-methyl propane sulfonate, ethylene sulfonate, sulfoethyl methacrylate and styrene sulfonate. Structures for these monomers are shown as follows:

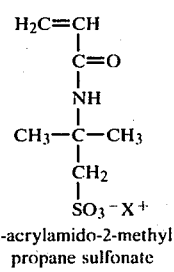

2-acrylamido-2-methyl
propane sulfonate

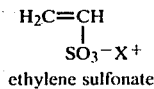

ethylene sulfonate

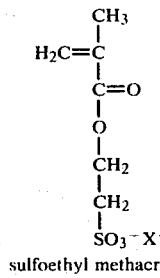

sulfoethyl methacrylate

Other suitable polymers may be produced by polymer derivitization to obtain a sulfonate-containing polymer as shown below:

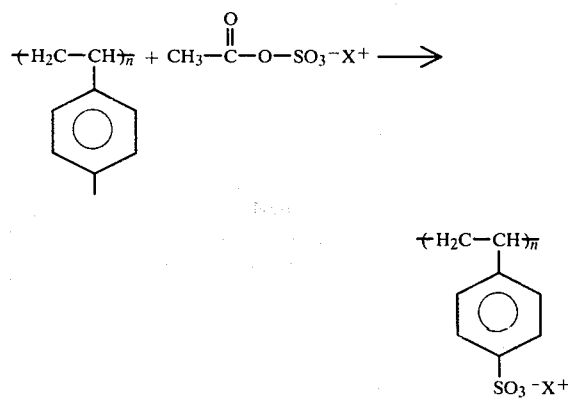

n: 2 to several million
$X^+$: alkaline earth metal such as Na, Ca, K, Li, etc: or a quaternary ammonium compound; or an ethoxylated amine such as soya bis(polyoxyethylene)$_{15}$amine.

As stated above, the monomers containing nitrogen salts of sulfonic acid may optionally be polymerized with a second monomer. Such second monomer may be neutral, anionic, or cationic.

Suitable neutral monomers include acrylamide, substituted acrylamide, vinyl acetate, polyvinyl alcohol derived by hydrolysis of polyvinyl acetate, vinyl pyrrolidone, N-vinyl acetamide, ethylene, styrene, acrylates, methacrylates, and admixtures thereof. Suitable acrylamides are set forth below:

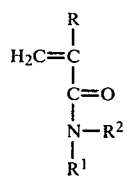

where; R = H, CH$_3$
R$^1$, R$^2$ = H, CH$_3$, CH$_2$OCH$_3$, CH$_2$OCH$_2$—CH(CH$_3$)CH$_3$,
(CH$_2$CH$_2$O)$_{\overline{x}}$H aryl groups, etc.
R$^1$—R$^2$ = cycloalkylene where; x = 1-50,

Acrylamides

Suitable acrylates are set forth below:

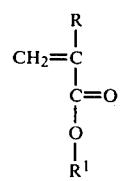

where; R = H, CH$_3$
R$^1$ = alkyl groups (C$_1$ to C$_{30}$), aryl groups, CH$_2$CH$_2$OH, (CH$_2$CH$_2$O)$_{\overline{x}}$H, etc.

where; x = 1-50

Acrylates

Suitable neutralized anionic monomers include acrylic acid, methacrylic acid, maleic acid, maleic acid esters, crotonic acid, vinyl phosphonate and admixtures thereof. Structures of several anionic monomers are set forth below:

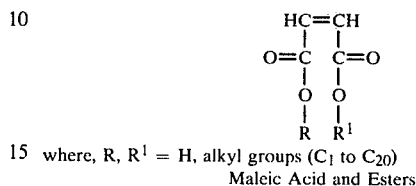

where, R, R$^1$ = H, alkyl groups (C$_1$ to C$_{20}$)
Maleic Acid and Esters

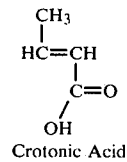
Crotonic Acid

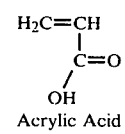
Acrylic Acid

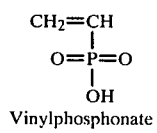
Vinylphosphonate

Suitable cationic monomers include vinyl amine, dimethylamino-ethyl methacrylate, vinyl pyridine, dimethyl diallyl ammonium chloride, methacrylamido propyl trimethyl ammonium chloride, vinyl benzyl trimethyl ammonium chloride, vinyl triphenyl phosphonium bromide, and admixtures thereof. Structures of several cationic monomers are set forth below:

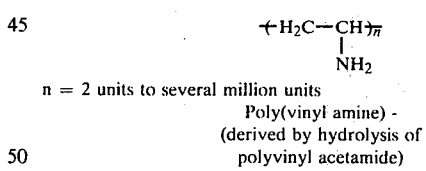

n = 2 units to several million units
Poly(vinyl amine) -
(derived by hydrolysis of
polyvinyl acetamide)

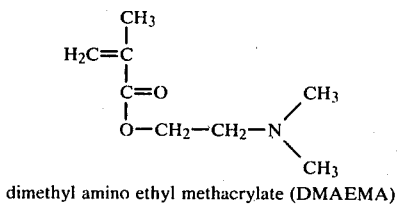
dimethyl amino ethyl methacrylate (DMAEMA)

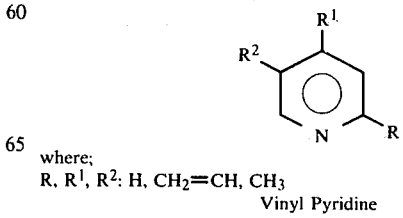
where;
R, R$^1$, R$^2$: H, CH$_2$=CH, CH$_3$
Vinyl Pyridine

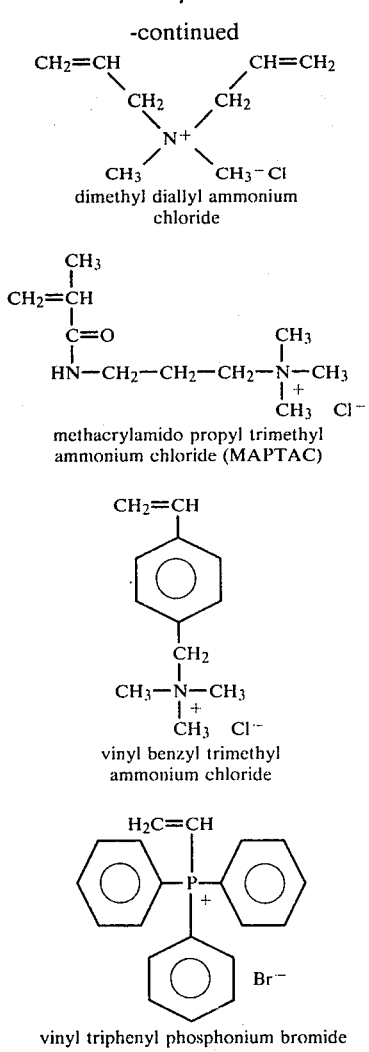

dimethyl diallyl ammonium chloride methacrylamido propyl trimethyl ammonium chloride (MAPTAC)

vinyl benzyl trimethyl ammonium chloride vinyl triphenyl phosphonium bromide

The polymers may be not only linear, but also may be segmental in nature. Multi-functional vinyl monomers, such as divinyl benzene or methylene bis acrylamide, may be used to promote branching of the sulfonate-containing polymers. Grafting of the sulfonate-containing monomer onto natural or synthetic polymers can be initiated by the use of ceric ammonium nitrate or benzoyl peroxide, for instance. A third approach would be to synthesize block copolymers which can be formed by the use of bifunctional initiators, e.g., di-t-butyl 4,4'-azobis(4-cyanoperoxyvalerate); or ceric ammonium nitrate-treated polyvinyl pyrrolidone (PVP) which results in triblock polymers, PVP being the center block.

The molecular weight of these polymers may be controlled by varying the amount of initiator, which could be any free radical initiator, such as ammonium persulfate, plus redox catalyst, if desired, or azobis-isobutyro nitrile (AIBN); by varying the amount of chain transfer agent such as $FeCl_3$, $NaHSO_3$, mercaptan, etc.; or by varying the temperature of reaction. The polymerization itself can be achieved by solution, suspension, or emulsion techniques.

The polymers composed of alkoxylated nitrogen salts of sulfonic acid containing monomers and the additional monomer may be of various mole ratios. Suitable ratios are from about 0.03 to 1.0 of the sulfonic acid monomers with the ethoxylated amine salt being present in a mole fraction of about 0.1 to 1.0. The preferred polymer of the invention is poly(acrylamide-(co)-AMPS) in a mole fraction of 9 acrylamide-1 Amps., which has been partially neutralized with soya bis(polyoxyethylene)$_{15}$amine. Such polymer is preferred because its addition leads to superior skin moisture retention and improved feel to skin during and after treatment.

To be useful as hair conditioners, the sulfonate containing polymers should not be in the free acid form. Several salts have demonstrated usefulness, e.g., ethoxylated quaternary ammonium and ethoxylated amine salts. Neutralization (10 to 100 mole %) of sulfonic acid containing polymer with an ethoxylated nitrogen containing salt has proven especially beneficial for improving skin conditioning properties; with 40 to 60 mole % being preferred to further optimize such conditioning properties.

The following examples and test results are believed to demonstrate the practice of the invention.

EXAMPLE 1

A one liter resin kettle with overhead stirrer, $N_2$ inlet, condenser, thermocouple, heating mantle, and provision for external cooling was set up in a hood. 24.5 g of AMPS (0.118 m) was dissolved in 118 ml of 1 N NaOH and the pH adjusted to 8, the total weight was 159.3 g. This solution was then added to the kettle along with 152.8 g of 49.4% Dow aqueous acrylamide (1.06 m) and 100 ml of $H_2O$. Then 0.038 g of $CuCl_2.2H_2O$ dissolved in 62 ml of $H_2O$ was added. Heating, stirring, and $N_2$ purging was performed. After about 40 minutes when, after reaching a temperature of 50° C., the heating mantle was removed and 0.50 g of $(NH_4)_2S_2O_8$ dissolved in 25 ml of $H_2O$ was added, the temperature fell to 46°–47° C. Within 5 minutes the exotherm started, the solution became thicker, and the $N_2$ flow was reduced and removed to the head space. The calculated heat of polymerization at room temperature was 22.5° C., based on a 25% aqueous acrylamide solution. External cooling was applied to maintain the temperature at or below 60° C. After completion of the exotherm, a temperature of 50° C. was maintained. A sample was removed after 2 hours for acrylamide analysis, the nitrogen turned off, and 0.63 g of $NaHSO_3$ (0.5 mole % based on acrylamide) dissolved in 25 ml of $H_2O$ was added. After stirring for an hour, vacuum was pulled for 1–3 minutes several times over about a 15 minute period to help remove excess $SO_2$. While stirring vigorously, 118 g (0.059 m) of soyabis(polyoxyethylene)$_{15}$amine was added with 75 ml of wash $H_2O$ over about 15 minutes period. After the additions, the pH was 8. Citric acid solution (25 g) was added to lower the pH to 6±0.5. The intrinsic viscosity of the polymer-sodium salt was 1.04 dl/g measured in 5.05 N NaCl at 29° C.

EXAMPLE 2

A 22 liter four-neck flask fitted with reflux condenser, nitrogen purge, thermocouple, stirrer was charged with 3,750 g (18.12 moles) of 2-acrylamido-2-methyl propane sulfonic acid (AMPS) from Lubrizol predissolved in 3,875 g of deionized water containing 0.375 g of $CuSO_4.5H_2O$ (0.0015 m) and $N_2$ purged. In rapid succession, the following were added with stirring at room temperature: 225 g of $(NH_4)_2S_2O_8$ (0.986 m) predissolved in 2,250 ml of $H_2O$, 0.375 g of $FeSO_4.7H_2O$ (0.0013 m) predissolved in 125 ml of $H_2O$, and 375 g of $NaHSO_3$ (3.6 m) predissolved in 750 ml of $H_2O$, and an additional 1,125 ml of $H_2O$. After 15 minutes, polymerization began as indicated by a 25° C. exotherm (20° to 45° C.). After 6 hours, the reaction product was neutralized with 750 g of NaOH (18.75 m) predissolved in 750 ml of H$_2$O. The product obtained was a clear yellow liquid having a Brookfield viscosity (#3, 6 rpm) of 1,400 cp at 35% polymer solids. Infrared spectrum confirmed the structure as poly(AMPS) with absorptions at 1650 cm$^{-1}$, 1550 cm$^{-1}$, 1220$^{-1}$, 1035$^{-1}$, and 615 cm$^{-1}$. 20 g of poly(AMPS) (0.09 moles) dissolved in 37 g H$_2$O was adjusted to pH 4.0 with citric acid. 66 g soya bis poly(oxyethylene)$_{15}$amine was then reacted and the pH adjusted to 6.5.

EXAMPLE 3

To a 500 ml resin kettle equipped with reflux condenser, stirrer, N$_2$ purge, and thermocouple was charged with 20 g of AMPS (0.097 m), 13.9 g of acrylic acid (0.193 m), and 40 ml of deionized H$_2$O. To this mixture was added 1.02 g of (NH$_4$)$_2$S$_2$O$_8$ (0.0045 m) predissolved in 10 ml of H$_2$O, 0.003 g of FeSO$_4$.7H$_2$O (2.2×10$^{-6}$ m) (100 ppm) predissolved in 10 ml of H$_2$O, and 1.7 g of NaHSO$_3$ (0.016 m) predissolved in 15 ml of H$_2$O. The reactants were N$_2$ purged for 5 minutes with stirring. After 15 minutes at room temperature (22° C.), the reaction exothermed to a maximum temperature of 41° C. After 2 hours, the reaction was terminated leaving clear viscous polymer solution of 30% solids. Infrared spectrum and % conversion data confirmed a 2/1 mole comonomer ratio in the resultant polymer. To 20 g of the above 30% solids solution was added 16.8 g of soya bis(polyoxyethylene)$_{15}$amine (0.034 m) at pH of 4.0. The pH was then adjusted to 6.5 with NaOH if needed.

EXAMPLE 4

54.03 g of AMPS (0.26 m) was neutralized with 10.44 g of NaOH (0.26 m) predissolved in 240 ml of deionized H$_2$O. To a 1500 ml resin kettle fitted with the standard equipment was added the AMPS monomer solution, 200 g of vinylacetamide (2.35 m) predissolved in 340 ml of deionized H$_2$O, and 2.54 g of azobis-isobutyronitrile (0.0132 m) predissolved in 40 ml of ethyl acetate. After N$_2$ purging, the reaction temperature was raised to 85° C. and maintained for 3 hours. The product was precipitated into acetone and dried in vacuo at 43° C. overnight. A white powder was obtained. Infrared spectrum confirmed copolymerization. 442.8 g of the 30% solids solution (1.36 m) and 29.26 g of 36% HCl (2.9 m) were charged into a 1000 ml round bottom flask equipped with a reflux condenser and refluxed for 22 hours. The polymeric product was precipitated into acetone and dried in vacuo at 45° C. for 24 hours. A brown solid polymer was obtained. Infrared spectrum confirmed hydrolysis. 3 g of poly(vinylamine-(co)-AMPS) was dissolved in 27 g H$_2$O with 9.6 g of soyabis(polyoxyethylene)$_{15}$amine at a pH of 4.0. After thorough mixing, the pH was raised to 7.

EXAMPLE 5

20 g of poly(AMPS) of Example 2 (0.030 mole) was adjusted to pH 6.5 with citric acid or NaOH as needed and 15.3 g (0.015 m) of methyl poly(oxyethylene)$_{15}$stearyl ammonium chloride added.

Each of the neutralized sulfonic acid-containing polymers prepared in the above Examples was evaluated as a skin conditioner. Specifically, each polymer was evaluated for feel during and after application. All polymers were evaluated in commercial liquid soaps and hand lotions. The test procedures are set forth below and the results recorded in Tables I through III.

Each polymer was evaluated sequentially for feel during use, feel during rinse off (if applicable), and feel after application. Performance was evaluated by independent observes on coded samples using rating of 1 to 5 (poor to excellent).

Each polymer (1 wt %) was blended with a commercial product and evaluated by feel. One hand of each observer was treated with 1 gram of commercial liquid soap and at the same time the other hand of each observer was treated with 1 gram of commercial product plus 1 wt % polymer. Simultaneously, the observers rated the feel of the products. For liquid soaps, the feel during wash, during rinse, and after treatment was evaluated. (Tables I & II). For hand lotions, both hands of each observer were treated with each formulation and compared to its previously evaluated untreated commercial hand lotion. The feel during application and after application was evaluated using again a rating of 1 to 5 (poor to excellent) (Table III).

In addition to feel, moisture vapor transmission rates (MVTR) were determined on the material of Example 1. 3 mil films on laboratory paper toweling were prepared with the material of Example 1. Each film was attached to a glass container holding a desiccant, anhydrous CaCl$_2$, and placed in 92 to 96% RH at 86° F. The MVTR results indicated a high rate of water vapor transmission.

The percent pickup of air moisture was also determined for the polymer of Example 1. A 2.2 mil film of Example 1 on laboratory paper toweling will pick up approximately 10 wt% at 86° F., 92° to 96° relative humidity in 24 hours. The laboratory paper, by itself, has essentially no pickup of air moisture. The polymer film has a soft smooth feel both dry and at 10 wt% water. This data indicates that the materials of the invention function as humectants as well as skin conditioners.

The liquid soaps were prepared by the following companies: Go-Jo Industries, Inc. (Tuff Soap, Le Soap) Akron, Ohio 44309; Yardley of London, Inc. (English Lavender), Chicago, Ill. 60611; Minnetonka, Inc. (Soft Soap), Minnetonka, Minn. 55343.

The hand lotions were prepared by the following companies: Cheesebrough Ponds Inc. (Vaseline Intensive Care), Greenwich, Conn. 06830; The Andrew Jergens Co. (Jergens Lotion), Cincinnati, Ohio 45214; and The J. B. Williams Company Inc. (Rose Milk); Cranford, N.J. 07016.

TABLE I

| Product | Ave. Feel During Wash[1] | Ave. Feel During Rinse[1] | Ave. After Feel[1] | Total Average[2] |
| --- | --- | --- | --- | --- |
| Tuff Soap by Go-Jo | 3.0 | 2.0 | 2.5 | 2.5 |
| Tuff Soap + 1% Ex. 1 (Solids) | 2.8 | 3.0 | 2.5 | 2.8 |
| Le Soap by Go-Jo | 3.0 | 2.3 | 2.8 | 2.7 |
| Le Soap + 1% Ex. 1 | 3.3 | 2.8 | 2.5 | 2.8 |
| English Lavender by Yardley | 3.0 | 3.0 | 3.8 | 3.3 |
| English Lavender + 1% Ex. 1 | 2.8 | 3.0 | 3.3 | 3.0 |
| Soft Soap | | | | |

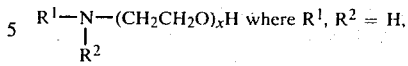

TABLE I-continued

Performance of Example 1 in Commercial Liquid Soaps

| Product | Ave. Feel During Wash[1] | Ave. Feel During Rinse[1] | Ave. After Feel[1] | Total Average[2] |
|---|---|---|---|---|
| by Minnetonka Soft Soap | 3.8 | 3.0 | 2.5 | 3.1 |
| + 1% Ex. 1 | 4.0 | 3.0 | 3.0/ 3.3 | |

[1] Evaluated by a ranking from 1 (poor) to 5 (excellent) by four independent observers. The rating shown is an average of the four observations.
[2] Total average is an average of the feel during wash, rinse, and after application.

TABLE II

Performance of Polymers in Tuff Soap by Go-Jo

| Product/Polymer | Ave. Feel During Wash[1] | Ave. Feel During Rinse[1] | Ave. After Feel[1] | Total Average[2] |
|---|---|---|---|---|
| Tuff Soap | 2.5 | 2.3 | 2.0 | 2.3 |
| + 1 wt % Ex. 1 (Solids) | 3.0 | 2.8 | 2.3 | 2.7 |
| + 1 wt % Ex. 2 | 3.5 | 2.8 | 2.5 | 2.9 |
| + 1 wt % Ex. 3 | 3.8 | 2.8 | 2.0 | 2.8 |
| + 1 wt % Ex. 4 | 2.5 | 3.0 | 2.5 | 2.7 |
| + wt % Ex. 5 | 4.0 | 3.3 | 2.5 | 3.3 |

[1] Evaluated by ranking from 1 (poor) to 5 (excellent) by four independent observers. The rating shown is an average of the four observations.
[2] Total average is an average of the feel during wash, rinse, and after application.

TABLE III

Performance of Polymers In Commercial Hand Lotions

| Product | Ave. Feel During Application | Ave. Feel After Application | Total Average |
|---|---|---|---|
| Vaseline Intensive Care by Chesebrough Ponds | 3.5 | 3.0 | 3.3 |
| Vaseline Intensive Care + 1 wt % Ex. 1 (solids) | 3.8 | 3.5 | 3.7 |
| + 1 wt % Ex. 2 | 4.0 | 4.0 | 4.0 |
| + 1 wt % Ex. 3 | 2.8 | 2.8 | 2.8 |
| + 1 wt Ex. 4 | 3.5 | 3.5 | 3.5 |
| + 1 wt % Ex. 5 | 3.5 | 3.8 | 3.7 |
| Jergens Lotion by the Andrew Jergens Co. | 2.8 | 3.3 | 3.0 |
| Jergens Lotion + 1 wt % Ex. 1 | 4.3 | 4.3 | 4.3 |
| + 1 wt % Ex. 2 | 4.0 | 3.8 | 3.9 |
| + 1 wt % Ex. 3 | 3.5 | 3.8 | 3.7 |
| + 1 wt % Ex. 4 | 1.3 | 2.8 | 1.8 |
| + 1 wt % Ex. 5 | 3.3 | 2.5 | 2.9 |
| Rose Milk by J. B. Williams Co. | 3.0 | 3.8 | 3.4 |
| Rose Milk + 1 wt % Ex. 1 | 4.8 | 4.0 | 4.4 |
| + 1 wt % Ex. 2 | 3.8 | 3.3 | 3.5 |
| + 1 wt % Ex. 3 | 3.3 | 3.5 | 3.4 |
| + 1 wt % Ex. 4 | 2.5 | 3.3 | 2.9 |
| + 1 wt % Ex. 5 | 3.3 | 3.5 | 3.4 |

I claim:

1. A method of conditioning skin, comprising: applying a composition containing from 0.1 to 10 wt.% of a polymer made from at least one ethylenically unsaturated addition polymerizable monomer containing an alkoxylated nitrogen salt of sulfonic acid and at least one additional monomer selected from the group consisting of neutral monomers, anionic monomers, or cationic monomers, to skin so as to obtain good conditioning properties; said addition polymerizable monomer being present in a mole fraction of about 0.03 to 1.0; said salt being derived from ethoxylated amine having the following structure:

$$R^1\text{—}N\text{—}(CH_2CH_2O)_xH \text{ where } R^1, R^2 = H,$$
$$|$$
$$R^2$$

alkyl ($C_1$-$C_{30}$), aryl $(CH_2CH_2O)_xH$, or $R^1$-$R^2$ = cycloalkylene and x = 1 to 50.

2. The method of claim 1 wherein: said polymerizable monomer comprises at least one ethylenically unsaturated addition polymerizable monomer containing an ethoxylated nitrogen salt of a sulfonic acid.

3. The method of claim 1, wherein: said additional monomer is a neutral monomer and is a member selected from the group consisting of acrylamide, substituted acrylamide, vinyl acetate, vinyl pyrrolidone, N-vinyl acetamide, ethylene, styrene, acrylate, and admixtures thereof.

4. The method of claim 1, wherein: said second monomer is a neutralized anionic monomer and is a member selected from the group consisting of acrylic acid, maleic acid, maleic acid esters, crotonic acid, vinyl phosphonate and admixtures thereof.

5. The method of claim 1, wherein: said second monomer is a cationic monomer and is a member selected from the group consisting of vinyl amine, dimethylamine-ethyl methacrylate, vinyl pyridine, dimethyl diallyl ammonium chloride, methacrylamido propyl trimethyl ammonium chloride, vinyl benzyl trimethyl ammonium chloride, vinyl triphenyl phosphonium bromide, and admixtures thereof.

6. The method of claim 1, wherein: said ethoxylated amine has the following structure:

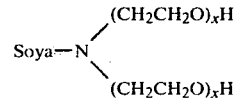

7. The method of claim 1, wherein: said polymerizable monomer comprises 2-acrylamido 2-methyl propane sulfonate.

8. The method of claim 7, wherein: said additional monomer comprises acrylamide.

9. The method of claim 8, wherein: said salt comprises soya bis(polyoxyethylene)$_{15}$amine.

10. The method of claim 9, wherein: said salt is present in a mole fraction of about 0.1 to 1.0.

11. The method of claim 10, wherein: said salt is present in a mole fraction of about 0.4 to 0.6.

12. A method of conditioning skin, comprising: applying a composition containing from 0.1 to 10 wt.% of a polymer made from at least one ethylenically unsaturated addition polymerizable monomer being present in a mole fraction of about 0.03 to 1.0 and containing an alkoxylated nitrogen salt of sulfonic acid to skin so as to obtain good conditioning properties; said salt being derived from an ethoxylated quaternary ammonium salt having the following structure:

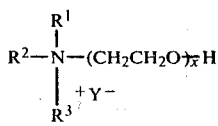

-continued where, $R^1, R^2, R^3$ = H,
   alkyl $(C_1-C_{30})$,
   aryl,
   $(CH_2CH_2O)_{\overline{x}}H$, or
$R^1-R^2$ = cycloalkylene,
where, Y = halide, sulfate,
   x = 1 to 50.

13. The method of claim 12, wherein: said polymer includes at least one additional monomer selected from the group consisting of neutral monomers, anionic monomers, cationic mnomers, or admixtures thereof.

14. The method of claim 12 or 13, wherein: said polymerizable monomer comprises at least one ethylenically unsaturated addition polymerizable monomer containing an ethoxylated nitrogen salt of a sulfonic acid.

15. The method of claim 13, wherein: said additional monomer is a neutral monomer and is a member selected from the group consisting of acrylamide, substituted acrylamide, vinyl acetate, vinyl pyrrolidone, N-vinyl acetamide, ethylene, styrene, acrylate, and admixtures thereof.

16. The method of claim 13, wherein: said second monomer is an anionic monomer and is a member selected from the group consisting of acrylic acid, maleic acid, maleic acid esters, crotonic acid, vinyl phosphonate and admixtures thereof.

17. The method of claim 13, wherein: said second monomer is a cationic monomer and is a member selected from the group consisting of vinyl amine, dimethylamino-ethyl methacrylate, vinyl pyridine, dimethyl diallyl ammonium chloride, methacrylamido propyl trimethyl ammonium chloride, vinyl benzyl trimethyl ammonium chloride, vinyl triphenyl phosphonium bromide, and admixtures thereof.

18. The method of claim 13, wherein: said polymerizable monomer comprises 2-acrylamido 2-methyl propane sulfonate.

19. The method of claim 18, wherein: said additional monomer comprises acrylamide.

20. The method of claim 19, wherein: said salt comprises soya bis(polyoxyethylene)$_{15}$amine.

21. The method of claim 20, wherein: said salt is present in a mole fraction of about 0.1 to 1.0.

22. The method of claim 21, wherein: said salt is present in a mole fraction of about 0.4 to 0.6.

* * * * *